(12) United States Patent
Schaldach et al.

(10) Patent No.: US 6,976,993 B2
(45) Date of Patent: Dec. 20, 2005

(54) STENT

(75) Inventors: Max Schaldach, deceased, late of Erlangen (DE); by Max Schaldach, Jr., legal representative, Berlin (DE); Daniel Lootz, Warnemuende (DE); Karsten Koop, Rostock (DE); Curt Kranz, Berlin (DE)

(73) Assignee: Biotronik Mess- und Therapiegeraete GmbH & Co., (DE)

( * ) Notice: Subject to any disclaimer, the term of this patent is extended or adjusted under 35 U.S.C. 154(b) by 0 days.

(21) Appl. No.: 09/974,780

(22) Filed: Oct. 9, 2001

(65) Prior Publication Data

US 2002/0042649 A1    Apr. 11, 2002

(30) Foreign Application Priority Data

Oct. 10, 2000   (DE) ............................... 100 50 971

(51) Int. Cl.[7] ............................................... A61F 2/06
(52) U.S. Cl. ..................... 623/1.15; 623/1.17
(58) Field of Search ............. 606/191–198; 623/1.15, 1.17, 1.11, 1.16

(56) References Cited

U.S. PATENT DOCUMENTS

| | | | | |
|---|---|---|---|---|
| 5,695,516 A | * | 12/1997 | Fischell et al. | 606/194 |
| 5,755,776 A | * | 5/1998 | Al-Saadon | 623/1.15 |
| 5,776,161 A | * | 7/1998 | Globerman | 606/194 |
| 5,776,183 A | * | 7/1998 | Kanesaka et al. | 623/1.15 |
| 5,836,964 A | * | 11/1998 | Richter et al. | 606/194 |
| 5,922,021 A | * | 7/1999 | Jang | 623/1.15 |
| 5,928,280 A | | 7/1999 | Hansen et al. | |
| 5,931,867 A | * | 8/1999 | Haindl | 623/1.15 |
| 5,972,018 A | * | 10/1999 | Israel et al. | 606/198 |
| 6,027,527 A | * | 2/2000 | Asano et al. | 623/1.15 |
| 6,193,747 B1 | * | 2/2001 | von Oepen | 623/1.15 |
| 6,261,319 B1 | * | 7/2001 | Kveen et al. | 623/1.15 |

(Continued)

FOREIGN PATENT DOCUMENTS

EP    928605    7/1999

(Continued)

*Primary Examiner*—Eduardo C. Robert
*Assistant Examiner*—Jessica R. Baxter
(74) *Attorney, Agent, or Firm*—Hahn Loeser & Parks, LLP; John J. Cunniff

(57) ABSTRACT

A stent, in particular a coronary stent, for expansion from a first condition into an expanded second condition in which it holds a vessel in an expanded state, comprising a tubular body whose peripheral surface (1) is formed by a number of support portions (2) which extend in the longitudinal direction of the stent and which comprise bar elements (3) which are connected by way of connecting bars (4), wherein there is provided a number of support portion groups (1.1) with at least a first support portion (2.1) and a second support portion (2.2, 2.3) in adjacent relationship in the peripheral direction of the stent, whose bar elements (3.1, 3.2, 3.3) extend in a meander configuration in the longitudinal direction of the stent, and wherein the first engagement points (4.1, 4.2) of first connecting bars (4) engage the first support portion (2.1) and the second engagement points (4.2, 4.4) of the first connecting bars (4) engage the second support portion (2.2, 2.3), wherein the first and second engagement points (4.1, 4.3, 4.2, 4.4) of the first connecting bars (4) are spaced from each other in the longitudinal direction of the stent and the first connecting bars (4) are of such a configuration and arrangement that the spacing between the first and second engagement points (4.1, 4.3, 4.2, 4.4) of the first connecting bars (4) in the longitudinal direction of the stent changes upon expansion of the stent to compensate for the reduction in length of the support portions.

38 Claims, 2 Drawing Sheets

U.S. PATENT DOCUMENTS 6,352,552 B1 * 3/2002 Levinson et al. .......... 623/1.15
2003/0004567 A1 * 1/2003 Boyle et al. ............... 623/1.16

FOREIGN PATENT DOCUMENTS

| EP | 0 937 442 A2 | 8/1999 |
| EP | 0 945 107 A2 | 9/1999 |
| WO | WO 98/32412 | 7/1998 |
| WO | WO98/40035 A1 | 9/1998 |
| WO | WO99/65421 A1 | 12/1999 |
| WO | WO00/42946 A1 | 7/2000 |

* cited by examiner

STENT

The present invention concerns a stent, in particular a coronary stent, for expansion from a first condition into an expanded second condition in which it holds a vessel in an expanded state, comprising a tubular body whose peripheral surface is formed by a number of support portions which extend in the longitudinal direction of the stent and comprise bar elements which are connected by way of connecting bars. That arrangement has a number of support portion groups with at least a first support portion and a second support portion in adjacent relationship in the peripheral direction of the stent, the bar elements thereof extending in a meander configuration in the longitudinal direction of the stent. In addition the first engagement points of first connecting bars engage the first support portion and the second engagement points of the first connecting bars engage the second support portion.

BACKGROUND OF THE ART

A stent is what is known as an intraluminal expansion element which is used to hold a vessel, for example a blood vessel, in the human or animal body, in an expanded state. For that purpose the stent is moved in a compressed first condition by means of a suitable catheter to the location in the vessel, which is to be held in the expanded state. When the implantation location is reached the stent is radially expanded into an expanded second condition. In the case of what are known as balloon-expansible stents the stent is expanded by means of a balloon catheter to such a degree that, by virtue of plastic deformation, even after removal of the balloon, it maintains its expanded second condition and thus supports the vessel. In the stents which are referred to as self-expanding the stent is held in a compressed first condition against a return force, for example by means of a sheathing catheter. That constriction is released at the implantation location so that the stent of its own accord assumes its expanded second condition.

A known stent of the general kind set forth is for example the Crown Palmaz-Schatz™ coronary stent from Cordis, Warren, N.J., US, in which bar elements extending in a meander configuration in the longitudinal direction of the stent are connected in the region of reversal or turning points of the bar elements by way of connecting bars which extend in the peripheral direction of the stent. Admittedly, those stents are relatively flexible by virtue of their design configuration with the bar elements extending in a meander configuration in the longitudinal direction of the stent, but they suffer from the disadvantage that they shorten in length to a relatively great degree upon being expanded from the first condition into the second condition. That is undesirable as in that case on the one hand they experience a change in position in the blood vessel and on the other hand, upon the reduction in length, under some circumstances considerable loadings can be applied to the blood vessel.

SUMMARY OF THE INVENTION

Therefore the object of the present invention is to provide a stent of the general kind set forth, which does not suffer from the above-indicated disadvantages or at least suffers therefrom to a lesser degree, and which in particular has a reduced reduction in length upon expansion.

Based on a stent as set forth in the classifying portion of claim 1, that object is attained by the features recited in the characterizing portion of claim 1.

The present invention is based on the technical teaching that a stent of the general kind set forth, with an at least reduced decrease in length upon expansion, is obtained if the first and second engagement points of the first connecting bars are spaced relative to each other in a first longitudinal direction of the stent and the first connecting bars are of such a configuration and arrangement that the spacing between the first and second engagement points of the first connecting bars in the first longitudinal direction changes upon expansion of the stent to compensate for the reduction in length of the support portions. In other words, that means that the first connecting bars are of such a configuration and arrangement that the inclination of the connecting line between the first and second engagement points of the first connecting bar changes with respect to the peripheral direction of the stent upon expansion of the stent.

Due to the change in spacing in accordance with the invention between the first engagement points of the connecting bars on the first support portion and the second engagement points of the connecting bars on the second support portion, the first support portion is displaced with respect to the second support portion in adjoining relationship in the peripheral direction, in the longitudinal direction of the stent. In that respect, in accordance with the invention, the displacements of the support portions in the support portion groups are so selected that a more or less substantial compensation effect for the reduction in length of the support portions upon expansion of the stent occurs over the stent periphery. In that respect the degree of such compensation is in accordance with the relationship of those displacements in the longitudinal direction in relation to the reduction in length of the bar elements. It will be appreciated that, by virtue of expansion of the stent, a more or less substantial change in spacing of the engagement points of the bar elements occurs in the peripheral direction of the stent.

The support portions are usually displaced relative to each alternately in the peripheral direction of the stent in the manner described. It will also be appreciated however that a plurality of support portions which occur in succession in the peripheral direction form blocks without such compensation. Those support portion blocks are then connected together in the manner in accordance with the invention. Accordingly they are displaced relative to each in block-wise manner in order once again to afford more or less substantial compensation generally over the stent. It will further be appreciated that a plurality of support portions or support portion blocks which occur in succession in the peripheral direction can be displaced in the same direction. It is then only necessary for further support portions or support portion blocks to be provided in the peripheral direction, as are displaced relative to each in the opposite direction. In order to avoid twisting or distortion those further support portions or support portion blocks would then be displaced relative to each by the same amount in the opposite direction.

As mentioned, the support portions are in many embodiments displaced relative to each alternately in the peripheral direction of the stent in the described manner. For that purpose at least the bar elements of a first support portion and of the two second support portions which are arranged in the peripheral direction at both sides of the first support portion extend in a meander configuration in the longitudinal direction of the stent and the first engagement points of the first connecting bars engage the first support portion and the second engagement points of the first connecting bars engage one of the second support portions. The first and second engagement points of the first connecting bars are spaced from each other in a first longitudinal direction of the stent and the first connecting bars in that case are of such a configuration and arrangement that the spacing between the first and second engagement points of the first connecting bars changes in the same manner in the first longitudinal direction upon expansion of the stent.

Due to the change in spacing in accordance with the invention in the same direction as between the first engagement points of the connecting bars on the first support portion and the second engagement points of the connecting bars on the second support portions disposed on both sides of the first support portion, the first support portion is displaced in the longitudinal direction of the stent with respect to the second support portions in adjoining relationship at both sides in the peripheral direction, whereby in dependence on the respective relationship of said displacement in the longitudinal direction, in relation to the reduction in length of the bar element, the situation involves a more or less substantial degree of compensation of the reduction in length for the entire stent. It will be appreciated that in that case, by virtue of the expansion of the stent, there is a more or less substantial change in spacing of the engagement points of the bar elements in the peripheral direction of the stent.

The change in spacing between the first engagement points of the connecting bars and the associated second engagement points of the connecting bars should take place in the same manner, that is to say the nature of the change in spacing is the same at both sides of the first support portion. It will be noted that in this respect the magnitudes of the change in spacing at both sides do not necessarily have to be the same. In this case the displacements in the longitudinal direction as between the individual bar elements over the entire periphery are typically so selected that an equalization effect occurs over the entire stent periphery in order to avoid distortion or twisting of the stent over its length. However, the changes in spacing at both sides are identical not only in terms of their variation in respect of time but also in terms of their magnitude. That provides for uniform compensation for the reduction in length, without entailing distortion or twisting of the stent.

The direction in which the change in spacing between the engagement points of the connecting bars takes place or whether possibly also there is a change in direction upon the change in spacing, is immaterial. Thus, the spacing between the first and second engagement points of the first connecting bars in the first longitudinal direction upon expansion of the stent can overall decrease or increase. It is only necessary for a suitably large change in spacing, in quantitative terms, to apply at the end of the expansion effect.

In many embodiments of the stent according to the invention the first engagement points and additionally or alternatively the second engagement points of the first connecting bars are arranged in the region of a reversal or turning point, in particular at the reversal or turning point, of the bar element in question, thereby affording the stent a particularly simple design configuration.

The first connecting bars may be of any desired configuration. However they are substantially straight as that gives a stent which is particularly simple to produce and which in addition has a deformation behavior which can be easily understood and which can be particularly well reproduced.

Variants of the stent according to the invention which are preferred because they are simple to manufacture are distinguished in that the connecting line between the first and second engagement points of the first connecting bars extends substantially in the longitudinal direction of the stent.

The bar elements extending in a meander configuration in the longitudinal direction are preferably of a periodic configuration. This configuration may have any curvature distributions. Thus for example a sinusoidal configuration is a possibility. Advantageous embodiments of the stent according to the invention are distinguished in that at least one support portion is formed by a bar element extending in a meander configuration in the longitudinal direction of the stent, wherein each two bar element portions which are in adjacent relationship in the longitudinal direction of the stent and which extend between the turning points form the limbs of a V-shape. That design configuration affords a particularly high degree of flexibility for the stent in relation to its longitudinal direction.

In this case the bar element portions which are arranged in a V-shape preferably include an angle of between 80° and 100°. In accordance with a further preferred feature that angle is about 90°. That provides a uniform structure for the stent with good deformation properties both in the longitudinal and in the peripheral directions.

Advantageous developments of the stent according to the invention provide that the bar elements of the first and second support portions are of substantially the same periodic configuration and the length of the first connecting bars is so selected that the adjacent bar elements in the first condition of the stent are displaced by up to a quarter period relative to each other in the longitudinal direction of the stent. In the expanded condition, that affords particularly uniform and good distribution of the support locations for the vessel.

The support locations for the vessel are distributed in a particularly advantageous manner because it is uniform in particular when the bar elements of the first and second support portions involve substantially the same periodic configuration and the length of the first connecting bars is so selected that the adjacent bar elements, in the second condition of the stent, extend substantially in phase relative to each other, with respect to the longitudinal direction of the stent.

In many variants of the stent according to the invention the bar elements are adapted to increase the flexibility of the stent. That can be effected in many known ways. In particular, that can preferably be achieved insofar as at least one support portion is formed by a bar element, the direction of curvature of which changes in the central region between two turning points, as that increases the level of flexibility of the individual portions of the bar element.

The present invention further concerns an arrangement comprising a catheter for stent implantation having a stent as set forth in one of the preceding claims. In this respect, depending on the nature of the stent, this may involve a balloon catheter on which the stent is mounted, for example crimped. Equally the catheter may involve a sheathing catheter in which a stent in the form of a self-expanding stent is held in its first condition.

BRIEF DESCRIPTION OF THE DRAWINGS

Further preferred configurations of the present invention are set forth in the appendant claims and the description hereinafter of preferred variants of the stent according to the invention, with reference to the accompanying drawings in which:

DETAILED DESCRIPTION OF THE INVENTION

Figure 1:
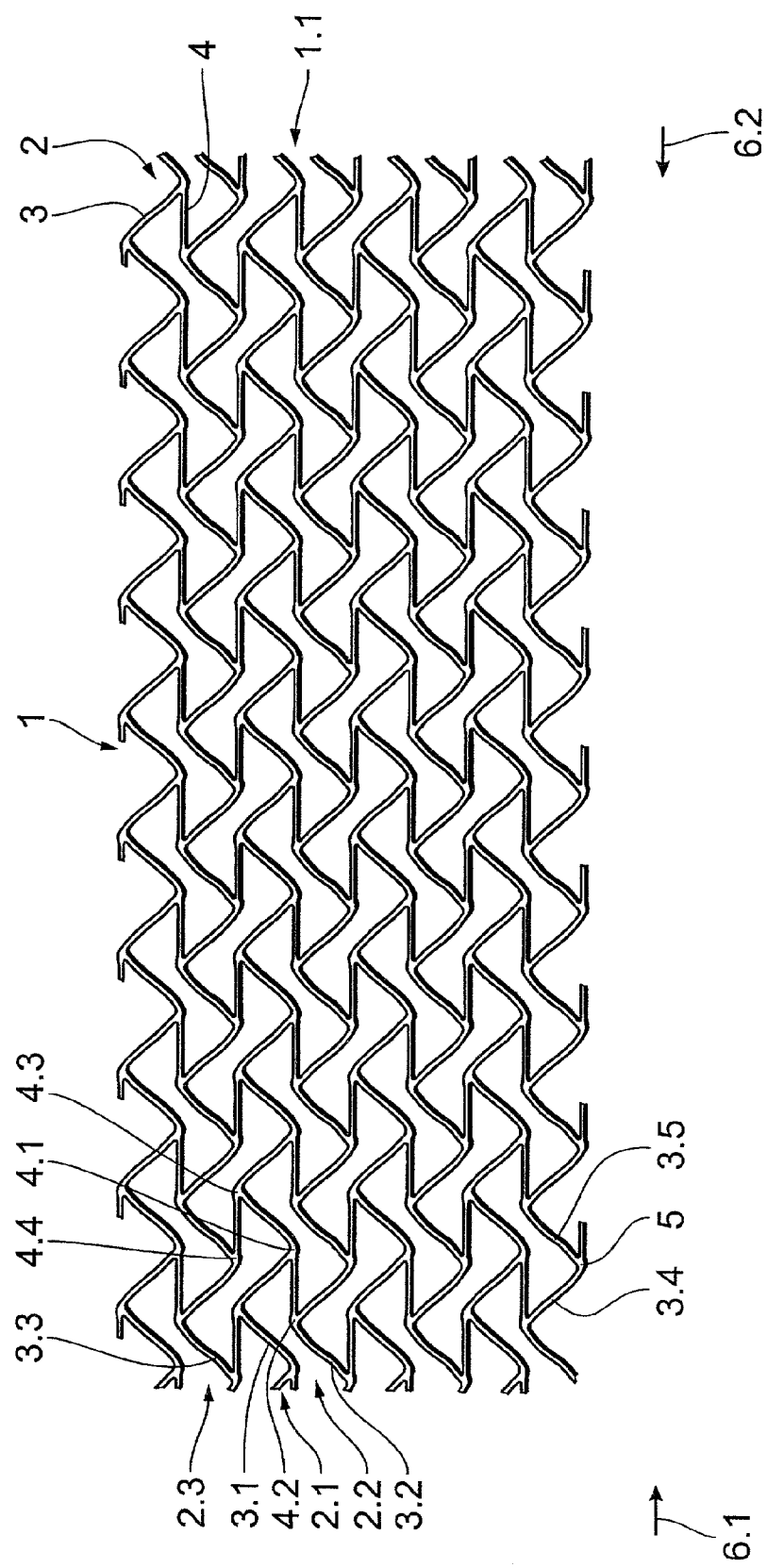
FIG. 1 is a plan view of the development of the peripheral surface of a preferred embodiment of the stent according to the invention.

FIG. 1 is a plan view of the development of the peripheral surface 1 of a preferred embodiment of the stent according to the invention, with support portions 2 formed by bar elements 3 extending in a meander configuration in the longitudinal direction of the stent. Those bar elements 3 are connected together in the peripheral direction of the stent by way of first connecting bars 4.

The stent has support portion groups 1.1 with a first support portion 2.1 and a second support portion 2.2 which is in adjacent relationship therewith in the peripheral direction, wherein the first engagement points 4.1 engage the first bar elements 3.1 of the first support portions 2.1 and the second engagement points 4.2 of the connecting bars 4 engage the second bar elements 3.2 of the second support portions 2.2. The connecting bars 4 each engage a respective reversal or turning point 5 of the bar element 3.

The connecting bars 4 extend rectilinearly in the longitudinal direction of the stent so that the first and second engagement points 4.1 and 4.2 of the connecting bars 4 are spaced relative to each in the longitudinal direction of the stent. Upon expansion of the stent into its enlarged second condition the orientation of the connecting bars 4 changes with respect to the peripheral direction of the stent. The inclination of the connecting bars 4 with respect to the peripheral direction of the stent decreases. That is also accompanied by a reduction in the spacing of the first engagement points 4.1 and the second engagement points 4.2, with respect to the longitudinal direction of the stent, so that the second bar element 3.2, that is to say of the second support portions 2.2, is displaced with respect to the first bar elements 3.1, that is to say with respect to the first support portion 2.1, in the first longitudinal direction 6.1.

That displacement between the first and second support portions 2.1 and 2.2 is so great that it compensates for the reduction in length of the bar elements 3.1 and 3.2 upon expansion of the stent, to the effect that the spacing in the longitudinal direction of the stent between the end region of the first bar element 3.1 in the first longitudinal direction 6.1 and the end region of the second bar element 3.2 in the opposite second longitudinal direction 6.2 in the expanded second condition corresponds to the spacing of those regions in the non-expanded first condition.

In order to prevent twisting or distortion of the stent upon expansion, adjoining the other side of the first bar element 3.1 is a further second bar element 3.3 forming a further second support portion 2.3. This is connected by way of connecting bars 4 to the first bar element 3.1, wherein the first engagement points 4.3 engage the first bar element 3.1 and the second engagement points 4.4 engage the second bar element 3.3. In that case, the connecting bars 4 are arranged in such a way that the first engagement points 4.1 and 4.3 are respectively spaced in the first direction 6.1 in relation to the associated second engagement points 4.2 and 4.4. The connecting bars 4 are of the same length so that this provides that the second bar elements 3.2 and 3.3 are not displaced relative to each upon expansion of the stent in the longitudinal direction of the stent as the spacing between the first engagement points 4.1, 4.3 and the second engagement points 4.2 and 4.4 respectively of the connecting bars changes in the same manner.

In the illustrated example the bar elements 3 and the connecting bars 4 are arranged in such a way that a first and a second bar element respectively alternate in the peripheral direction. That provides for distortion-free compensation in respect of the reduction in length. It will be appreciated however that different configurations can also be provided in other variants of the stent according to the invention. Thus for example instead of a first support portion comprising a single bar element it is possible for the stent to have support portions comprising a plurality of bar elements which adjoin each other in the peripheral direction and which are not designed or connected in the described manner. Then however the first support portions can again be connected in the described manner by way of suitable connecting bars to second support portions which adjoin at both sides and which are possibly of a corresponding design configuration so that overall once again this arrangement affords suitable distortion-free compensation for the reduction in length.

The bar elements 3 extend periodically in the longitudinal direction of the stent, wherein each two bar element portions 3.4 and 3.5 which are adjacent in the longitudinal direction of the stent and which extend between the turning points 5 form the limbs of a V-shape. In this arrangement the bar element portions 3.4 and 3.5 include an angle of 90°. The selected configuration means that the stent is particularly simple to manufacture. In addition this configuration affords particularly good flexibility for the stent with respect to its longitudinal axis.

The length of the connecting bars 4 is so selected that the adjacent bar elements 3.1, 3.2 and 3.3, in the expanded condition of the stent, extend in phase relationship with each other, with respect to the longitudinal direction of the stent. For that purpose, the length of the connecting bars 4 is so selected that the first and second bar elements 3.1 and 3.2 or 3.3 respectively in the illustrated first condition of the stent are arranged displaced relative to each other in the longitudinal direction by approximately a tenth of their period.

The bar elements 3 are also adapted to increase the flexibility of the stent, insofar as their direction of curvature in the central region between two turning points 5 changes. This slightly S-shaped configuration affords a lower level of stiffness of the bar elements in relation to forces acting in the longitudinal direction of the stent and thus gives the stent enhanced flexibility.

Figure 2:
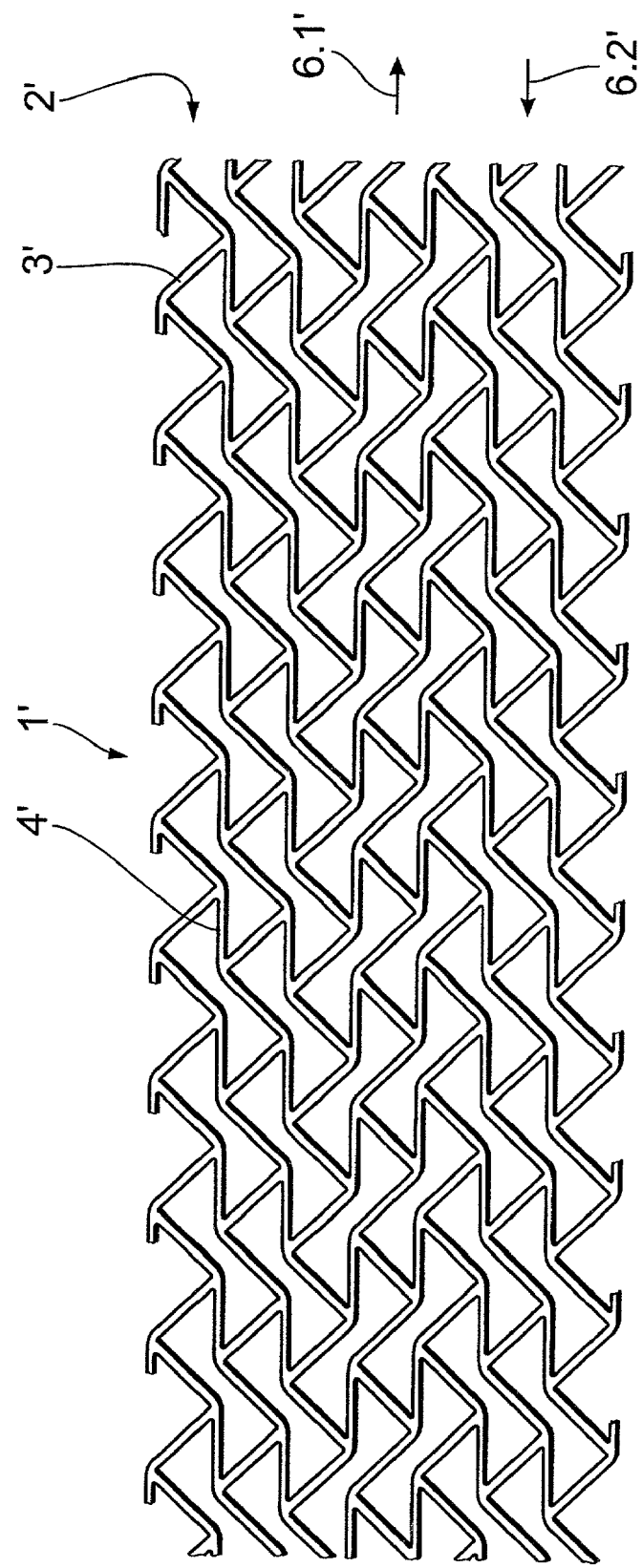
FIG. 2 is a plan view of the development of the peripheral surface of a further preferred embodiment of the stent according to the invention.

FIG. 2 is a diagrammatic plan view of the development of the peripheral surface 1' of a preferred embodiment of the stent according to the invention with support portions 2' which are formed by bar elements 3' extending in a meander configuration in the longitudinal direction of the stent. The bar elements 3' are connected together in the peripheral direction of the stent by way of first connecting bars 4'.

This variant does not differ in terms of its fundamental structure and its fundamental mode of operation from that shown in FIG. 1 so that only the differences will be discussed here. The difference is that the connecting bars 4' are arranged in such a way that, upon expansion of the stent, adjacent bar elements 3' are respectively displaced in pairs in the same first longitudinal direction 6.1' while the next two bar elements 3' which adjoin in the peripheral direction are both respectively displaced in the opposite second direction 6.2. In that arrangement there are so many pairs of bar elements 3' that the stent involves twist-free length compensation overall over the periphery of the stent.

It will be appreciated that other variants may also have a different number of mutually adjoining bar elements which are respectively displaced in the same longitudinal direction.

What is claimed is:

1. A stent, in particular a coronary stent, for expansion from a first condition into an expanded second condition in which it holds a vessel in an expanded state, said stent comprising:

a tubular body, a peripheral surface of which is formed by a plurality of support portions that extend in a longitudinal direction of the stent, the support portions comprising: a plurality of bar elements wherein each end of each bar element, excepting bar elements on the ends of the tubular body, connects to an adjacent bar element, forming an angle of between 80° and 100°; and a plurality of connecting bars extending substantially rectilinearly in the longitudinal direction of the stent that connect the bar elements;

wherein the support portions form a plurality of support portion groups with at least a first support portion and a second support portion in adjacent relationship thereto in a peripheral direction of the stent, the bar elements of which extend in a meander configuration in the longitudinal direction of the stent, and wherein a first engagement point of the connecting bars engages the first support portion and a second engagement point of the connecting bars engages the second support portion, such that the first and second engagement points are spaced apart from each other in the longitudinal direction of the stent and the connecting bars are configured and arranged so the spacing in the longitudinal direction between the first and second engagement points decreases upon expansion of the stent to compensate for a reduction in length of the respective support portions.

2. The stent of claim 1, wherein at least the bar elements of a first support portion and of the two second support portions arranged in the peripheral direction of the stent at both sides of the first support portion extend in a meander configuration in the longitudinal direction of the stent and the first engagement points of the connecting bars engage the first support portion and the second engagement points of the connecting bars engage one of the two second support portions, wherein the first and second engagement points are spaced relative to each other in the longitudinal direction of the stent and the connecting bars are configured and arranged so that the spacing in the longitudinal direction of the stent changes between the first and second engagement points decreases upon expansion of the stent in the same manner.

3. The stent of claim 2, wherein at least the first engagement points of the connecting bars are located near a turning point of the bar element to which the connecting point is engaged.

4. The stent of claim 3, wherein the second engagement points of the connecting bars are located near a turning point of the bar element to which the connecting point is engaged.

5. The stent of claim 4, wherein the connecting bars are of a substantially straight configuration.

6. The stent of claim 5, wherein a connecting line between the first and second engagement points extends substantially in the longitudinal direction of the stent.

7. The stent of claim 6, wherein the bar elements of the first and second support portions are of substantially the same periodic configuration and a length of the connecting bars is such that the adjacent bar elements in the first condition of the stent are displaced relative to each by up to a quarter period in the longitudinal direction of the stent.

8. The stent of claim 7, wherein the bar elements of the first and second support portions are of substantially the same period configuration and a length of the connecting bars is such that in the second condition of the stent the adjacent bar elements extend substantially in phase with each other with respect to the longitudinal direction of the stent.

9. The stent of claim 8, wherein the bar elements are designed to increase the flexibility of the stent.

10. The stent of claim 2, wherein the connecting bars are of a substantially straight configuration.

11. The stent of claim 10, wherein a connecting line between the first and second engagement points extends substantially in the longitudinal direction of the stent.

12. The stent of claim 11, wherein the bar elements of the first and second support portions are of substantially the same periodic configuration and a length of the connecting bars is such that the adjacent bar elements in the first condition of the stent are displaced relative to each by up to a quarter period in the longitudinal direction of the stent.

13. The stent of claim 12, wherein the bar elements of the first and second support portions are of substantially the same period configuration and a length of the connecting bars is such that in the second condition of the stent the adjacent bar elements extend substantially in phase with each other with respect to the longitudinal direction of the stent.

14. The stent of claim 13, wherein the bar elements are designed to increase the flexibility of the stent.

15. The stent of claim 1, wherein at least the first engagement points of the connecting bars are located near a turning point of the bar element to which the connecting point is engaged.

16. The stent of claim 15, wherein the second engagement points of the connecting bars are located near a turning point of the bar element to which the connecting point is engaged.

17. The stent of claim 16, wherein the connecting bars are of a substantially straight configuration.

18. The stent of claim 17, wherein a connecting line between the first and second engagement points extends substantially in the longitudinal direction of the stent.

19. The stent of claim 18, wherein the bar elements of the first and second support portions are of substantially the same periodic configuration and a length of the connecting bars is such that the adjacent bar elements in the first condition of the stent are displaced relative to each by up to a quarter period in the longitudinal direction of the stent.

20. The stent of claim 19, wherein the bar elements of the first and second support portions are of substantially the same period configuration and a length of the connecting bars is such that in the second condition of the stent the adjacent bar elements extend substantially in phase with each other with respect to the longitudinal direction of the stent.

21. The stent of claim 20, wherein the bar elements are designed to increase the flexibility of the stent.

22. The stent of claim 1, wherein the connecting bars are of a substantially straight configuration.

23. The stent of claim 22, wherein a connecting line between the first and second engagement points extends substantially in the longitudinal direction of the stent.

24. The stent of claim 23, wherein the bar elements of the first and second support portions are of substantially the same periodic configuration and a length of the connecting bars is such that the adjacent bar elements in the first condition of the stent are displaced relative to each by up to a quarter period in the longitudinal direction of the stent.

25. The stent of claim 24, wherein the bar elements of the first and second support portions are of substantially the same period configuration and a length of the connecting bars is such that in the second condition of the stent the adjacent bar elements extend substantially in phase with each other with respect to the longitudinal direction of the stent.

26. The stent of claim 25, wherein the bar elements are designed to increase the flexibility of the stent.

27. The stent of claim 1, wherein a connecting line between the first and second engagement points extends substantially in the longitudinal direction of the stent.

28. The stent of claim 27, wherein the bar elements of the first and second support portions are of substantially the same periodic configuration and a length of the connecting bars is such that the adjacent bar elements in the first condition of the stent are displaced relative to each by up to a quarter period in the longitudinal direction of the stent.

29. The stent of claim 28, wherein the bar elements of the first and second support portions are of substantially the same period configuration and a length of the connecting bars is such that in the second condition of the stent the adjacent bar elements extend substantially in phase with each other with respect to the longitudinal direction of the stent.

30. The stent of claim 29, wherein the bar elements are designed to increase the flexibility of the stent.

31. The stent of claim 1, wherein the bar elements of the first and second support portions are of substantially the same periodic configuration and a length of the connecting bars is such that the adjacent bar elements in the first condition of the stent are displaced relative to each by up to a quarter period in the longitudinal direction of the stent.

32. The stent of claim 31, wherein the bar elements of the first and second support portions are of substantially the same period configuration and a length of the connecting bars is such that in the second condition of the stent the adjacent bar elements extend substantially in phase with each other with respect to the longitudinal direction of the stent.

33. The stent of claim 32, wherein the bar elements are designed to increase the flexibility of the stent.

34. The stent of claim 1, wherein the bar elements of the first and second support portions are of substantially the same period configuration and a length of the connecting bars is such that in the second condition of the stent the adjacent bar elements extend substantially in phase with each other with respect to the longitudinal direction of the stent.

35. The stent of claim 34, wherein the bar elements are designed to increase the flexibility of the stent.

36. The stent of claim 1, wherein the bar elements are designed to increase the flexibility of the stent.

37. The stent of claim 1, wherein at least one support portion formed by a bar element, the direction of curvature of which changes in a central region between a pair of turning points.

38. A catheter for stent implantation, said catheter comprising:
    a stent for expansion from a first condition into an expanded second condition in which it holds a vessel in an expanded state, said stent comprising:
    a tubular body, a peripheral surface of which is formed by a plurality of support portions that extend in a longitudinal direction of the stent, the support portions comprising:
    a plurality of bar elements wherein each end of each bar element, excepting bar elements on the ends of the tubular body, connects to an adjacent bar element, forming an angle of between 80° and 100°; and
    a plurality of connecting bars extending substantially rectilinearly in the longitudinal direction of the stent that connect the bar elements;
    wherein the support portions form a plurality of support portion groups with at least a first support portion and a second support portion in adjacent relationship thereto in a peripheral direction of the stent, the bar elements of which extend in a meander configuration in the longitudinal direction of the stent, and
    wherein a first engagement point of the connecting bars engages the first support portion and a second engagement point of the connecting bars engages the second support portion, such that the first and second engagement points are spaced apart from each other in the longitudinal direction of the stent and the connecting bars are configured and arranged so the spacing in the longitudinal direction between the first and second engagement points decreases upon expansion of the stent to compensate for a reduction in length of the respective support portions.

* * * * *